(12) United States Patent
Schneider

(10) Patent No.: US 11,197,604 B2
(45) Date of Patent: Dec. 14, 2021

(54) MOBILE PHONE CORNEA PLACIDO DISC IMAGE

(71) Applicant: Mark Schneider, Corona, CA (US)

(72) Inventor: Mark Schneider, Corona, CA (US)

( * ) Notice: Subject to any disclaimer, the term of this patent is extended or adjusted under 35 U.S.C. 154(b) by 288 days.

(21) Appl. No.: 16/541,976

(22) Filed: Aug. 15, 2019

(65) Prior Publication Data

US 2020/0107719 A1 Apr. 9, 2020

Related U.S. Application Data

(60) Provisional application No. 62/742,071, filed on Oct. 5, 2018.

(51) Int. Cl.
*A61B 3/107* (2006.01)
*H04M 1/02* (2006.01)
*A61B 3/00* (2006.01)
*A61B 3/14* (2006.01)

(52) U.S. Cl.
CPC ............ *A61B 3/107* (2013.01); *A61B 3/0008* (2013.01); *A61B 3/14* (2013.01); *H04M 1/0252* (2013.01)

(58) Field of Classification Search
CPC ......... A61B 3/107; A61B 3/0008; A61B 3/14; H04M 1/0252; H04M 1/0264; G03B 2215/0575; G03B 15/03; G03B 17/565; G03B 29/00
See application file for complete search history.

(56) References Cited

U.S. PATENT DOCUMENTS

| | | | |
|---|---|---|---|
| 4,993,826 A | 2/1991 | Yoder, Jr. | |
| 5,062,702 A | 11/1991 | Bille | |
| 5,526,072 A | 6/1996 | El Hage | |
| 5,526,073 A | 6/1996 | Mattioli | |
| 5,684,562 A | 11/1997 | Fujieda | |
| 6,152,565 A | 11/2000 | Liu | |
| 6,224,213 B1 | 5/2001 | Kobayashi | |
| 6,382,796 B1 * | 5/2002 | Ban ........................ | A61B 3/107 351/212 |
| 6,601,956 B1 * | 8/2003 | Jean ........................ | A61B 3/102 351/212 |
| 6,634,750 B2 | 10/2003 | Neal | |
| 6,634,752 B2 | 10/2003 | Curatu | |
| 6,974,215 B2 | 12/2005 | Hayashi | |
| 7,370,969 B2 | 5/2008 | Klyce et al. | |
| 7,467,870 B2 | 12/2008 | van de Kraats | |
| 7,661,820 B2 | 2/2010 | Hara | |
| 7,976,163 B2 | 7/2011 | Campbell et al. | |
| 8,602,033 B2 | 12/2013 | Jones | |

(Continued)

*Primary Examiner* — Mohammed A Hasan
(74) *Attorney, Agent, or Firm* — Kirk A. Buhler; Buhler & Associates Patenting

(57) ABSTRACT

Improvements in capturing an image of a cornea with Placido's disk lines is disclosed. The imaging is with a clam shell clamping device that is easily clamped onto a cellular device and the lighting tube is centered on the camera so the image at the end of the tube can be captured. The clamping device includes a ring light source that illuminates the outside of the tube. The tube has a plurality of geometrically spaced light and dark rings to create evenly spaced rings on the cornea. Imperfections in the cornea will distort the rings. The camera can capture the image and the image or picture can be forwarded to a doctor or other care giver to determine the perfection or imperfection of the cornea.

20 Claims, 5 Drawing Sheets

(56) References Cited

U.S. PATENT DOCUMENTS

| | | |
|---|---|---|
| 8,740,795 B2 | 6/2014 | Norris |
| 9,615,739 B2 | 4/2017 | Farrer et al. |
| 9,839,352 B2 | 12/2017 | Wallace et al. |
| 2010/0245585 A1* | 9/2010 | Fisher ................ H04M 1/0266 348/164 |
| 2012/0050683 A1 | 3/2012 | Yates |
| 2013/0070203 A1 | 3/2013 | Michaels et al. |
| 2013/0128223 A1 | 5/2013 | Wood et al. |
| 2015/0313462 A1 | 11/2015 | Reis |
| 2016/0000322 A1 | 1/2016 | Farrer et al. |
| 2016/0198946 A1 | 7/2016 | Zhou |
| 2018/0092534 A1 | 4/2018 | Nabhan |

* cited by examiner

| Angle Tot | Tan | Displaced above Tube Calc Length | Ring Height | Focus Dia | | |
|---|---|---|---|---|---|---|
| 0 | 0.000 | 0.000 | 0 | 0.650 | | |
| 4 | 0.070 | 0.038 | 0.038 | 0.648 | Black | 1 |
| 8 | 0.140 | 0.077 | 0.039 | 0.644 | White | 1 |
| 12 | 0.212 | 0.117 | 0.040 | 0.636 | Black | 2 |
| 16 | 0.287 | 0.158 | 0.041 | 0.625 | White | 2 |
| 20 | 0.364 | 0.200 | 0.042 | 0.611 | Black | 3 |
| 24 | 0.445 | 0.245 | 0.045 | 0.594 | White | 3 |
| 28 | 0.531 | 0.292 | 0.048 | 0.574 | Black | 4 |
| 32 | 0.624 | 0.343 | 0.051 | 0.551 | White | 4 |
| 36 | 0.726 | 0.399 | 0.056 | 0.526 | Black | 5 |
| 40 | 0.838 | 0.461 | 0.062 | 0.498 | White | 5 |
| 44 | 0.965 | 0.531 | 0.070 | 0.468 | Black | 6 |
| 48 | 1.110 | 0.610 | 0.080 | 0.435 | White | 6 |
| 52 | 1.279 | 0.703 | 0.093 | 0.400 | Black | 7 |
| 56 | 1.481 | 0.815 | 0.111 | 0.364 | White | 7 |
| 60 | 1.730 | 0.951 | 0.137 | 0.325 | Black | 8 |
| 64 | 2.047 | 1.126 | 0.175 | 0.285 | White | 8 |
| 68 | 2.471 | 1.359 | 0.233 | 0.244 | Black | 9 |
| 72 | 3.071 | 1.689 | 0.330 | 0.201 | White | 9 |

MOBILE PHONE CORNEA PLACIDO DISC IMAGE

CROSS REFERENCE TO RELATED APPLICATIONS

This application claims the benefit of Provisional Application Ser. No. 62/742,071 filed Oct. 5, 2018 the entire contents of which is hereby expressly incorporated by reference herein.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

This invention relates to improvements in a cornea imaging with a cell phone. More particularly, the present cell phone cornea Placido imaging allows a person with a cellular phone to capture an image of their cornea.

Description of Related Art Including Information Disclosed Under 37 CFR 1.97 and 1.98

A number of patents and or publications have been made to address these issues. Exemplary examples of patents and or publication that try to address this/these problem(s) are identified and discussed below.

U.S. Pat. No. 4,993,826 issued on Feb. 19, 1991 to Paul R. Yoder Jr. and is titled Topography Measuring Apparatus. This patent discloses a contour measuring apparatus and method of using the same is disclosed to measure the three-dimensional contour of a surface. Structure is provided to direct first light beams onto the surface being measured. Reflections of the first light beams from the surface are received for generating electrical output signals corresponding to electro-optically measurable optical images U.S. Pat. No. 5,526,072 issued on Jun. 11, 1996 to Sami G. El Hage and is titled Apparatus and technique for automatic centering and focusing a corneal topographer. This patent discloses a corneal topographer including a directional light source, a CCD and a positioning stage all controlled by a computer for automatically centering and focusing the corneal image onto the CCD. The computer receives video signals from the CCD representing the corneal image, which is digitized and displayed on a real-time basis on a monitor screen. A reflection of the directional light source is positioned to align in the center of the corneal image. An operator moves an optics head to place the corneal image on the monitor screen, roughly focuses the image, and then commands the computer to take over.

U.S. Publication Number 2018/0092534 was published on Apr. 5, 2018 to Tareq Issam Nabhan and is titled System and Method for Ophthalmological Imaging Adapted to a Mobile Processing Device. This publication discloses a system and method for ophthalmological imaging is provided for use with a mobile processing device, wherein the mobile processing device comprises a camera lens, light source, and processor configured to process images captured, received, and/or delivered by the mobile processing device. The mobile processing device adapted ophthalmological instrument system comprises housing segments, circuitry, lights, and a frustum cone, wherein the frustum cone comprises reference lines of a plurality of circular, frusto-conical, alternating transparent and opaque concentric rings in the conical surface in optical alignment with the mobile processing device's camera lens and subject's central cornea and/or tear-film layer(s).

What is needed is a device that can be clamped onto most cell phones to capture an image of the shape of the cornea. The proposed cell phone cornea Placido imaging disclosed in this document provides the solution.

BRIEF SUMMARY OF THE INVENTION

It is an object of the cell phone cornea Placido imaging to easily be installed and removed onto a cell phone, mobile device or any device with an integrated camera.

It is an object of the cell phone cornea Placido imaging for the cell phone to be able to transmit the image to a doctor or other person that can evaluate the stored image.

It is another object of the cell phone cornea Placido imaging to include an integrated lighting system to provide consistence and even illumination.

It is still another object of the cell phone cornea Placido imaging to utilize a blocking tube that interrupts the light form the illumination source.

Various objects, features, aspects, and advantages of the present invention will become more apparent from the following detailed description of preferred embodiments of the invention, along with the accompanying drawings in which like numerals represent like components.

BRIEF DESCRIPTION OF THE SEVERAL VIEWS OF THE DRAWING(S)

DETAILED DESCRIPTION OF THE INVENTION

Figure 1:
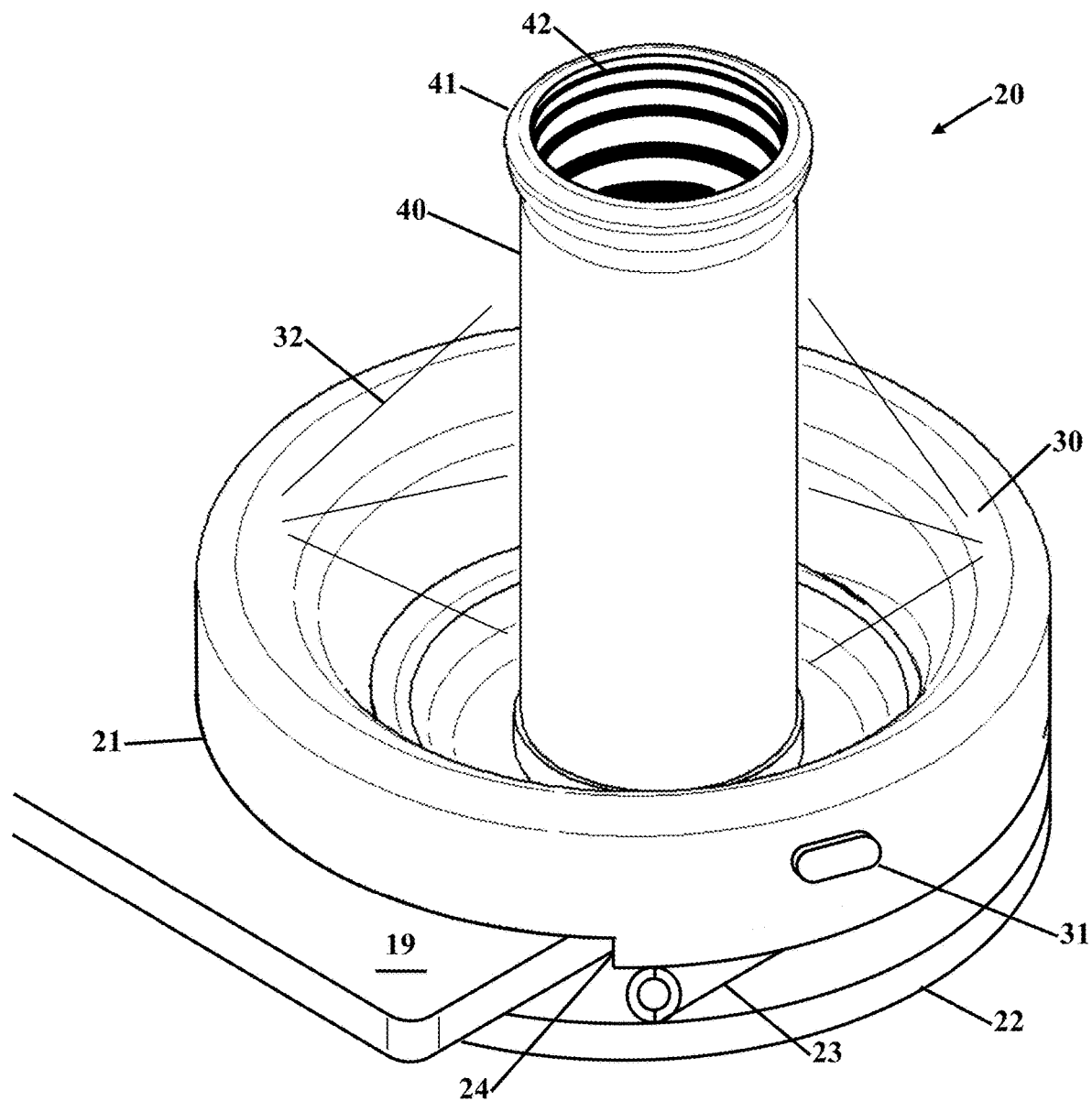
FIG. 1 shows a top perspective view of the Placido imaging on a cell phone.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, but is merely representative of various embodiments of the invention. The illustrated embodiments of the invention will be best understood by reference to the drawings, wherein like parts are designated by like numerals throughout.

| Item Numbers and Description | |
|---|---|
| 12 camera | 14 eye |
| 15 lens offset | 16 cornea diameter |
| 17 cornea | 18 pupil size |
| 19 cell phone | 20 Placido imaging device |
| 21 upper clam shell | 22 lower clam shell |
| 23 hinge | 24 step |
| 25 adjustable opening | 26 opening |
| 27 pad | 30 light ring |
| 31 switch | 32 light ray(s) |
| 33 outer ring projection | 34 inner ring projection |
| 35 lens center of curvature | 40 tube |
| 41 eyepiece | 42 rings |
| 43 target | 44 camera opening |
| 45 eyepiece | 97 in and out |
| 98 push | 99 close |

Several issues need to be resolved to provide a consistent reliable image so an average person with a cell phone can take an acceptable image. The multitude of cell phones with different cameras and different camera locations presents a first issue to be resolved. Nearly all cell phones and cellular devices have two cameras, one higher resolution camera in the rear of the phone and one lower resolution phone in the front of the phone. The low-resolution camera in the front of the phone is usually placed near an outer edge of the screen, while the higher resolution camera can be located in any position, including the center back of the cell phone. While making a device to accommodate any camera location can be accomplished by increasing the size of the proposed design, using the front facing low resolution camera on the edge of the phone will provide an image of sufficient resolution to determine the roundness of the cornea.

The second issue is providing an even lighting to eliminate or overcome ambient light. In the preferred embodiment the cornea is illuminated with the equivalent of a ring light that sends light in one direction to the cornea. Testing has identified that the cell phone camera determines focus location and brightness based upon locating an essentially flat image at a distance from the lens of the cell phone. Proper illumination of the cornea at a distance within the focal length of the cell phone camera results in cell phone camera finding the surface of the cornea, setting the focus length to the cornea and identifying the optimal contrast for a consistent image. This is all performed within most cell phones with the cell phone cornea Placido imaging disclosed in this document. The brightness of the illumination can have more than one level of illumination. The different levels of illumination can be adjusted based upon eye color and/or dilation of the pupil.

Figure 2:
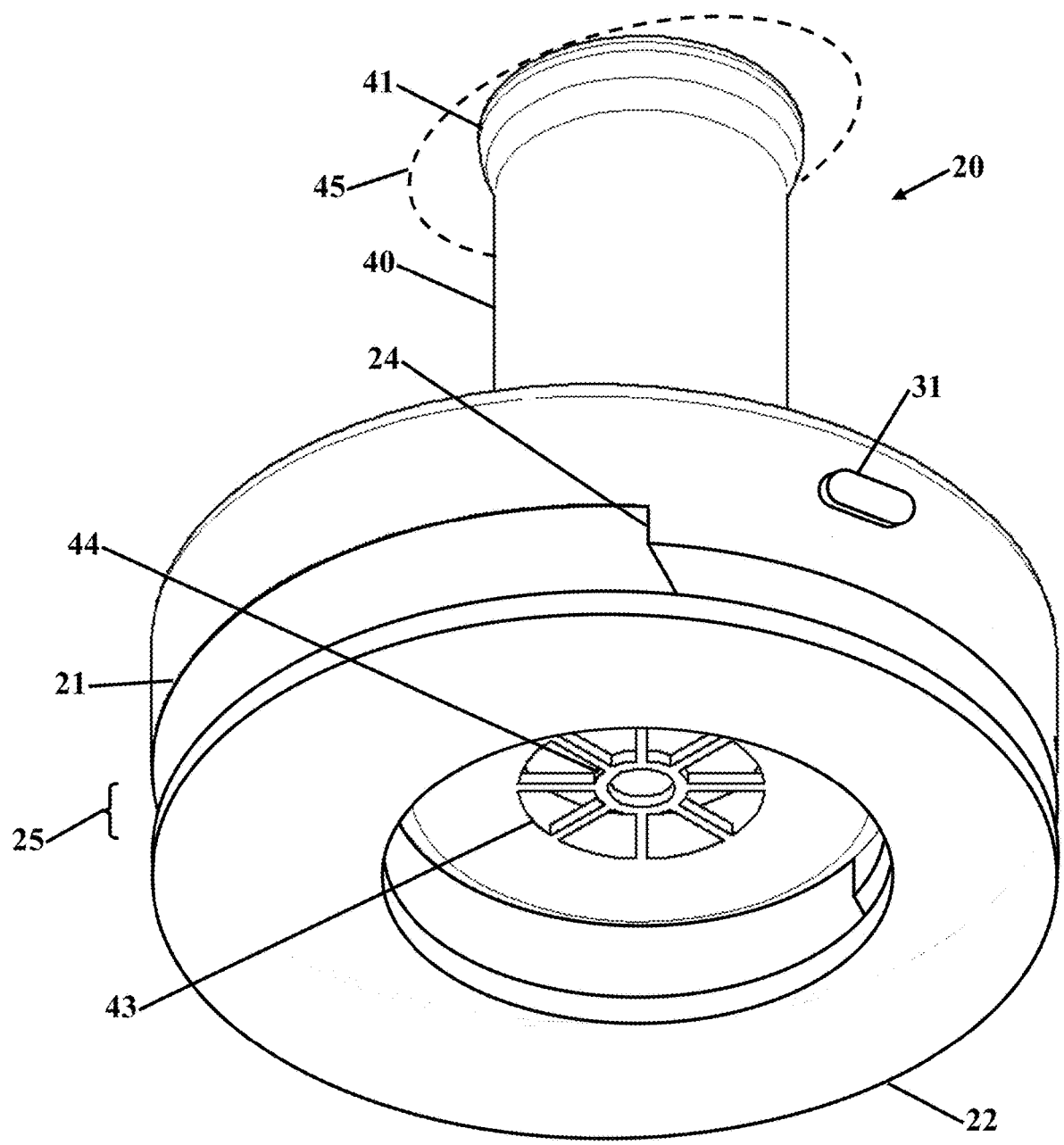
FIG. 2 shows a bottom perspective view of the Placido imaging for a cell phone.

FIG. 1 shows a top perspective view of the Placido imaging device 20 on a cell phone 19 and FIG. 2 shows a bottom perspective view of the Placido imaging device 20 for a cell phone. The Placido imaging device 20 clamps onto a cell phone 19 in a clam shell design where there is an upper clam shell 21 portion that hinges with a hinge 23 mechanism on a lower clam shell 22. In this embodiment there is a step 24 that limits how far the Placido imaging device 20 can be placed over the cell phone 19 and also provides a location for batteries that power illumination of the Placido imaging device 20.

The upper clam shell 21 and the lower clam shell 22 hinge to open the clam shell to accept the cell phone therein between. The clam shell portions allow the device to be easily installed, positioned and removed from the cell phone. They further allow for easy adjustment and position on nearly all cell phones, tablets and other similar mobile devices with a camera. Generally, most cell phones have a thickness of between 0.35 and 0.2 inches in thickness and the Placido imaging device 20 accommodates the different thicknesses in the clam shell adjustable opening 25.

In this embodiment the Placido imaging device 20 has an illumination ring type light source or light ring 30. Testing has identified that the light ring 30 provides a more consistent and even illumination, but in some ambient lighting conditions the rings 42 can provide an image on the cornea. The light ring 30 has a switch 31 that can provide a single level of illumination or multiple levels of illumination. The light ring 30 has a sufficient number of lights to provide an even illumination onto the tube 40. The light from the light ring 30 passes through the light ring 30 housing and through the tube 40. Within the tube 40 are light and dark bands that cast an image onto the cornea when an eye is placed on the eyepiece 42.

In FIG. 2 the bottom surface of the lower clam shell 21 is visible. The bottom surface shows a target 43 and a camera opening 44. These features provide three functions. First, it assists a person to locate the camera lens in the center of the target. Second, the open nature of the target 43 allows a person to see a larger amount of the phone to make it easier to determine the position of the cell phone camera relative to the central camera opening. Third, it provides a focal point for the user to determine where to look through the end of the tube 40. In an ideal situation the cell phone camera lens needs to be centered in the tube 40 and the eye of the user needs to look straight into the lens of the camera. In these conditions the only limit to a good picture is the movement of the user when the picture is taken. Some other variables can be the user placing the eye in a position that is not centered in the eyepiece 40. Typically, a non-centered eye is visible in the picture. While a round eyepiece is shown it is also contemplated that the eyepiece 45 can be contoured to assist the user to center the eye within the tube 40.

Figure 3:
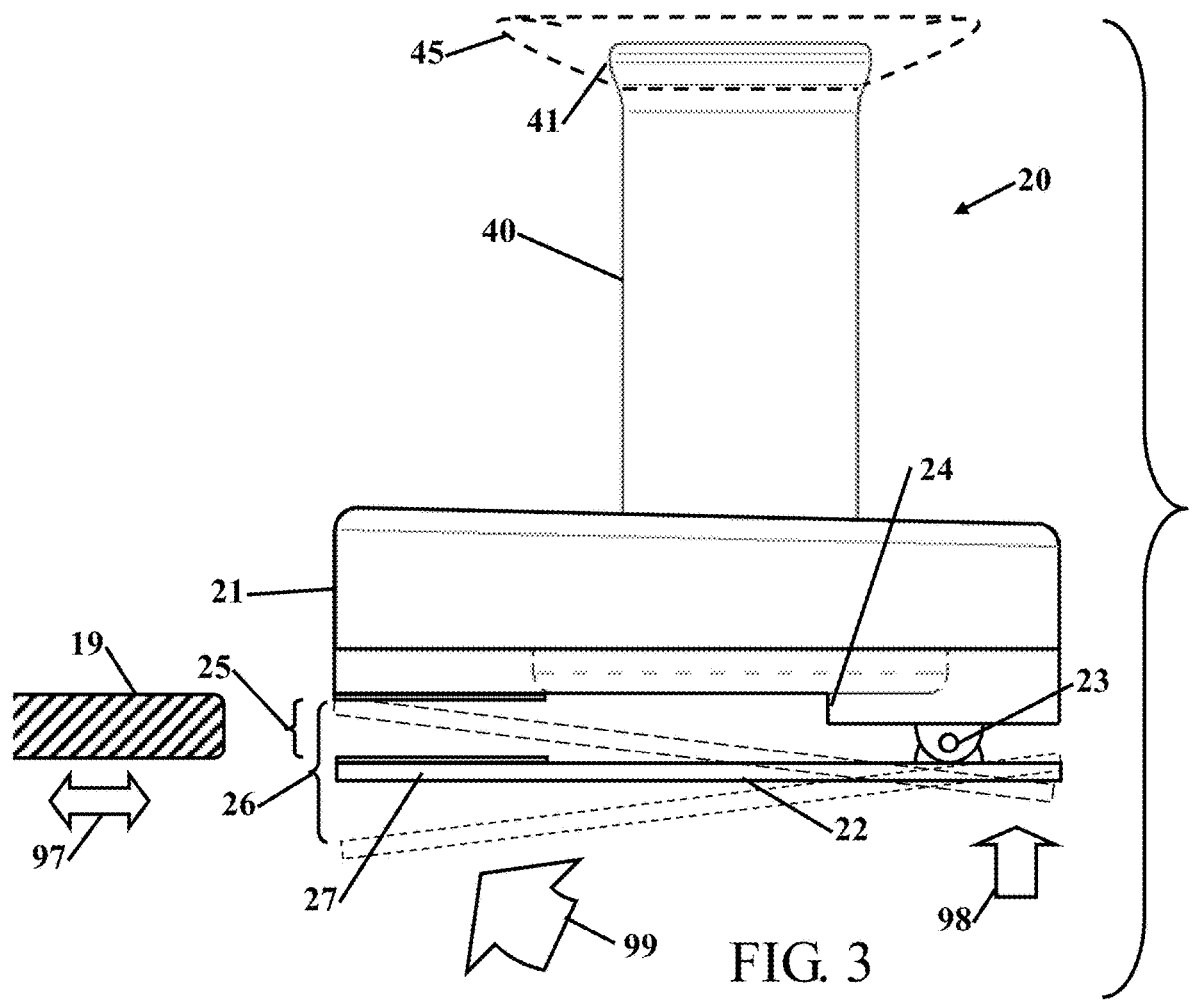
FIG. 3 shows a side view of the Placido imaging for a cell phone.

FIG. 3 shows a side view of the Placido imaging for a cell phone 19. To install a cell phone 19 the back of the two clam shells 21/22 and squeezed to pivot the hinge 24 to open the opposing side of the clam shell. A spring in the hinge 23 operates to close the clam shell and clamp an object, such as a cell phone 19 therein between 25. The opening 26 is the clam shell housing can accommodate a variety of thickness of cell phones 19 and can also accommodate cell phones 19 that are installed in a case without removing the case to use the Placido imaging device 20. Once the clam shells are opened the cell phone 19 can be moved in, out 97, up to the stop 24 or side-to-side to center the camera within the tube 40. One or a plurality of pads 27 frictionally hold the position of the Placido imaging device 20 on the cell phone 19.

Figure 4:
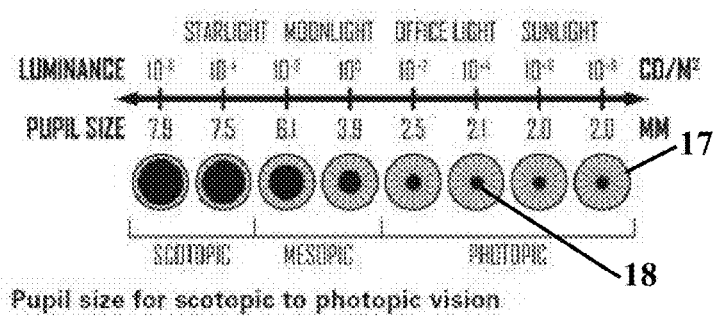
FIG. 4 shows a chart of pupil size based upon light intensity.

FIG. 4 shows a chart of pupil size based upon light intensity. Optimal image of the cornea image 17 is obtained when the pupil size is properly obtained. In the preferred embodiment the optimal lighting to the eye is between office lighting and sunlight. The ring light intensity along with the amount of light that passes into the tube 40 is set based upon the light intensity, material properties of the tube 40 and the thickness of the materials that are used.

Figures 5, 6:
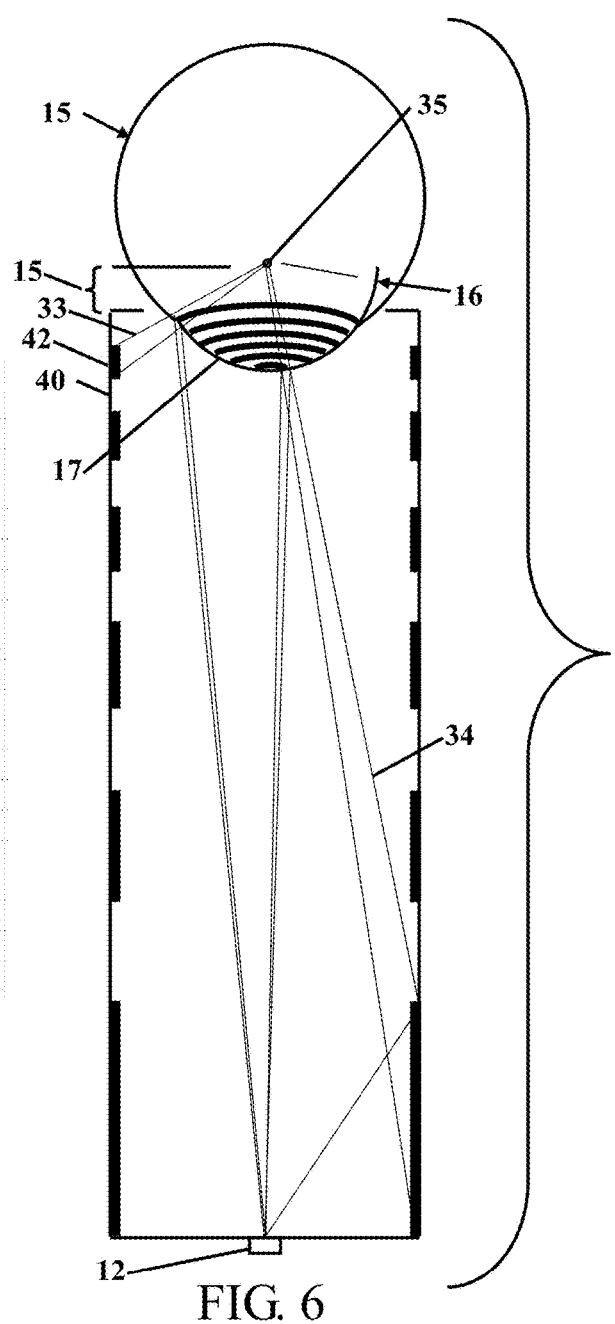
FIG. 5 shows a chart of ring height based upon distance from the lens.
FIG. 6 shows a tube with rings that reflect from the cornea into the camera of a cell phone to create a Placido image.

FIG. 5 shows a chart of ring height based upon distance from the lens and FIG. 6 shows a tube with rings that reflect from the cornea into the camera of a cell phone to create a Placido image. To project a consistence and even spacing of light and dark rings 42 onto the cornea 17. The geometry and relationship of the camera 12, tube 40 and cornea 17 are determined. While every eye 15 and cornea 17 can be different, the eye is generally about 1 inch in diameter and the diameter 16 cornea 17 is about 0.7 inches. Using a tube diameter of 1 inch the lens center of curvature 35 of the cornea is located at a distance of about 0.15 inches above the upper rim of the tube 40. Using this relationship, the location and thicknesses of the rings 42 can be calculated as shown in the table figure.

The height of the tube 40 is determined based upon the minimum focus distance for the camera 12. While a focus distance of 2 inches or less is possible with some cell phone cameras, a tube length of 3 inches is sufficient for the front camera of most cell phones and mobile devices with cameras. The outer ring projection 33 and the inner ring projection 34 is shown in the figure being projected through the tube 40, onto the cornea 17 as imaged in the camera 12.

In the table a step angle of 4 degrees is used to project (essentially) 9 light and dark rings, but using a different step angle can form more or less rings using the same tube diameter and length. Adjusting the distance from the lens offset 15 will also cause changes to the height and location of the rings 42. While a conical, elliptical, square or other shape tube 40 can be used, the ring 42 geometry can be calculated. In the preferred embodiment the rings 42 are evenly spaced light and dark solid rings, the rings can be created to form an image at most of the visible cornea surface. In addition, the projected image can be dots, dashes or other even words. Because the preferred embodiment is a round tube 40, the rings can be printed on film or other transparent or translucent material and can be interchangeably inserted into the inside diameter of the tube 40.

Figure 7:
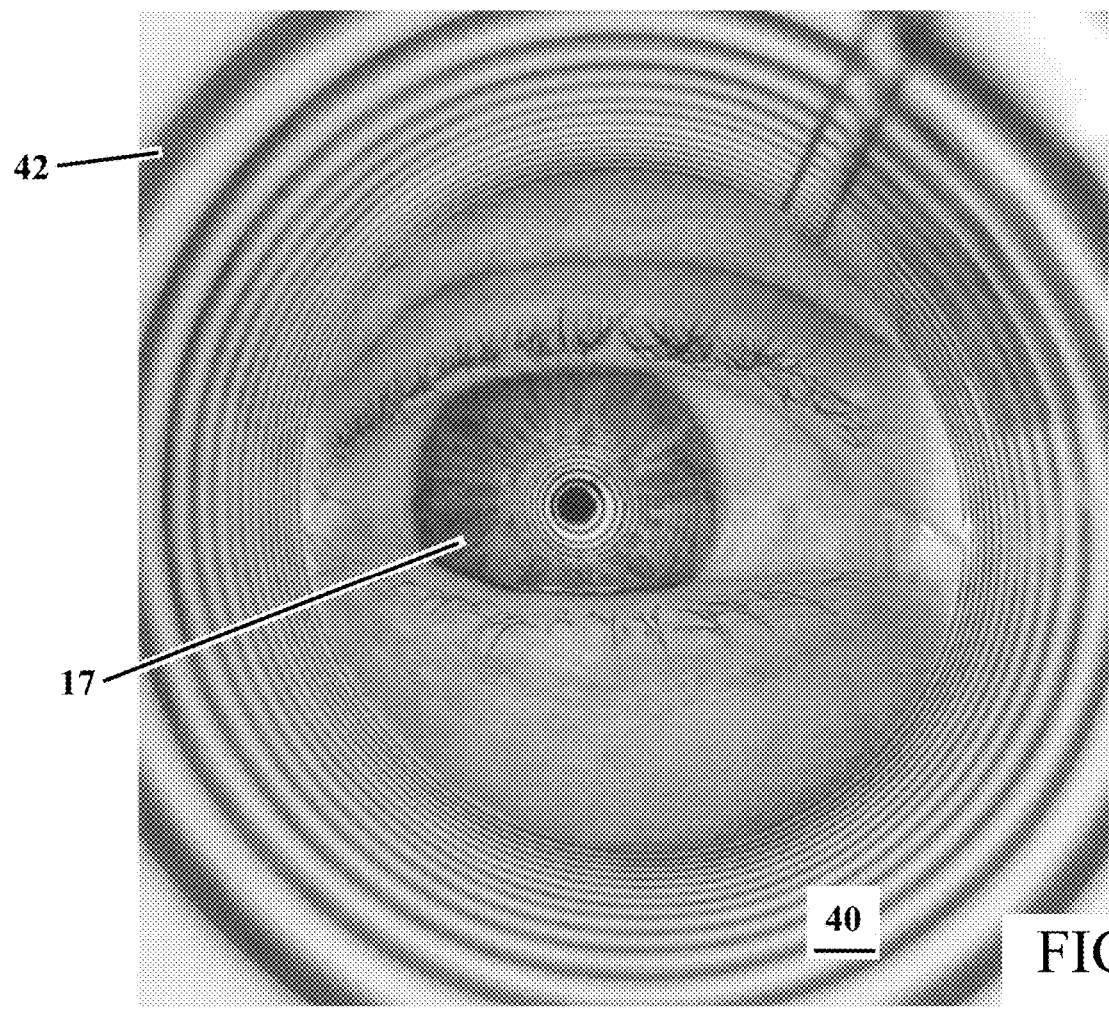
FIG. 7 shows the Placido image from a cell phone camera looking through the tube.
Figure 8:
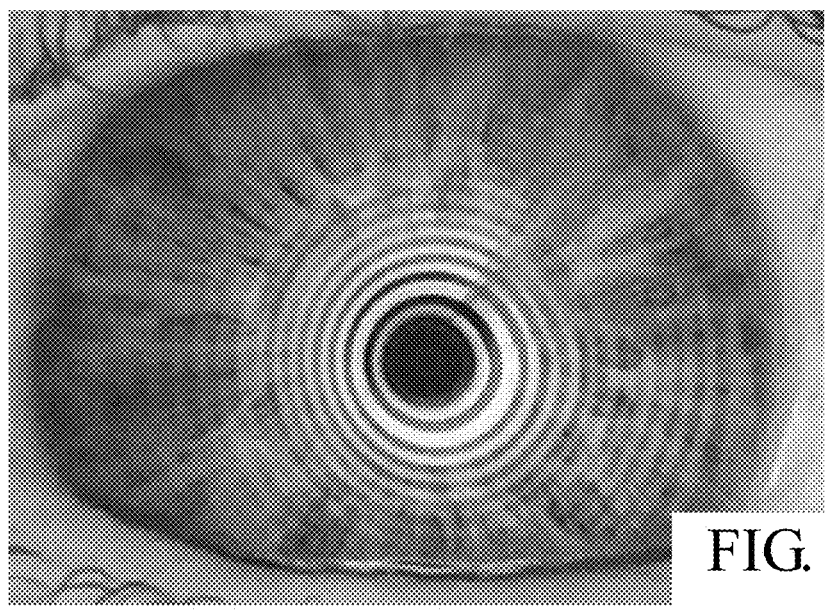
FIG. 8 shows the resulting image reflected off of the cornea.

FIG. 7 shows the Placido image from a cell phone camera looking through the tube 40 and FIG. 8 shows the resulting image of the ring(s) 42 reflected off of the cornea 17. In this image about 12 rings are shown with a ring step of 2.5 degrees per ring change. It should be noted that an imperfection in the film placed within the tube 40 is reflected in the 1 to 2 o'clock region of the cornea.

The captured image can then be processed with filters that turn the color image into black and white rings that define the edges of the rings. Further processing can also intemperate the roundness of the rings and the concentricity of the rings to determine if further action can or should be taken.

Thus, specific embodiments of a cell phone cornea Placido imaging have been disclosed. It should be apparent, however, to those skilled in the art that many more modifications besides those described are possible without departing from the inventive concepts herein. The inventive subject matter, therefore, is not to be restricted except in the spirit of the appended claims.

The invention claimed is:

1. A cell phone cornea Placido imaging comprising:
   a clam shell clamping mechanism that is configured to clamp a mobile communication device with a camera within said clam shell clamping mechanism over said camera in said mobile communication device;
   said clam shell clamping mechanism further includes an illuminating ring that produces light that is directed away from said clam shell clamping mechanism;
   said illuminating ring further includes a tube that extends from a first end of said illuminating ring, and
   said tube includes a plurality of light and dark rings whereby said light and dark rings project circular images in a curved surface placed at a second end of said tube.

2. The cell phone cornea Placido imaging according to claim 1, wherein said curved surface is an eye.

3. The cell phone cornea Placido imaging according to claim 1, wherein said second end of said tube has an eyepiece.

4. The cell phone cornea Placido imaging according to claim 1, wherein said first end of said tube has a centering orifice for centering said tube over said camera in said mobile communication device.

5. The cell phone cornea Placido imaging according to claim 1, wherein said light and dark rings are sized and spaced based upon the radius of curvature of said curved surface.

6. The cell phone cornea Placido imaging according to claim 1, wherein said illuminating ring has more than one level of brightness.

7. The cell phone cornea Placido imaging according to claim 6, wherein said more than one level of brightness is adjusted based upon an eye color.

8. The cell phone cornea Placido imaging according to claim 6, wherein said more than one level of brightness is adjustable based upon dilation of a pupil.

9. The cell phone cornea Placido imaging according to claim 1, wherein said first end of said tube has a target.

10. The cell phone cornea Placido imaging according to claim 9, wherein said target is configured as a focal point for an eye that centers said eye within said plurality of light and dark rings.

11. The cell phone cornea Placido imaging according to claim 9, wherein said target has a central opening that is configured for centering said plurality of light and dark rings on said camera.

12. The cell phone cornea Placido imaging according to claim 9, wherein said target has a central opening that is configured for centering said plurality of light and dark rings onto said curved surface.

13. The cell phone cornea Placido imaging according to claim 1, wherein said tube is transparent or translucent.

14. The cell phone cornea Placido imaging according to claim 1, wherein said plurality of light and dark rings are formed on a printed film located within said tube.

15. The cell phone cornea Placido imaging according to claim 1, wherein said plurality of light and dark rings are formed on a printed film located on an exterior of said tube.

16. The cell phone cornea Placido imaging according to claim 1, wherein said curved surface is spherical.

17. The cell phone cornea Placido imaging according to claim 1, wherein said mobile communication device is a cell phone, a music player, a tablet of a computer.

18. The cell phone cornea Placido imaging according to claim 1, wherein said illuminating ring is a plurality of light emitting diodes.

19. The cell phone cornea Placido imaging according to claim 1, wherein said plurality of light and dark rings captured on said camera are reflections of said light and dark rings on said curved surface.

20. The cell phone cornea Placido imaging according to claim 1, wherein said light rings are clear.

* * * * *